US008030616B2

(12) United States Patent
Nishino et al.

(10) Patent No.: US 8,030,616 B2
(45) Date of Patent: Oct. 4, 2011

(54) RADIATION IMAGE CAPTURING SYSTEM, SORTING APPARATUS FOR SORTING IMAGE CAPTURING INSTRUCTION INFORMATION, PROGRAM AND RADIATION IMAGE CAPTURING METHOD

(75) Inventors: Naoyuki Nishino, Minami-ashigara (JP); Naoki Mochizuki, Minami-ashigara (JP); Daiki Harada, Minami-ashigara (JP); Hiroshi Fukuda, Minato-ku (JP); Eiichi Kito, Minami-ashigara (JP); Yasunori Ohta, Yokohama (JP)

(73) Assignee: FUJIFILM Corporation, Tokyo (JP)

( * ) Notice: Subject to any disclaimer, the term of this patent is extended or adjusted under 35 U.S.C. 154(b) by 54 days.

(21) Appl. No.: 12/389,988

(22) Filed: Feb. 20, 2009

(65) Prior Publication Data
US 2009/0218494 A1 Sep. 3, 2009

(30) Foreign Application Priority Data

Feb. 28, 2008 (JP) ................................. 2008-048364
Feb. 13, 2009 (JP) ................................. 2009-031183

(51) Int. Cl.
*G01T 1/20* (2006.01)
(52) U.S. Cl. ................................................ 250/361 R
(58) Field of Classification Search ............... 250/336.1, 250/361 R, 580, 581, 582, 584, 362, 589; 718/102
See application file for complete search history.

(56) References Cited

U.S. PATENT DOCUMENTS

| 6,859,513 | B2 * | 2/2005 | Sako | 378/16 |
| 2001/0041832 | A1 | 11/2001 | Hirai | |
| 2004/0071263 | A1 * | 4/2004 | Motoki | 378/98 |
| 2005/0206967 | A1 | 9/2005 | Viswanth et al. | |

FOREIGN PATENT DOCUMENTS

| EP | 1 251 683 A1 | 10/2002 |
| JP | 2000-105297 A | 4/2000 |
| JP | 2001-340326 A | 12/2001 |
| JP | 3494683 B2 | 11/2003 |
| JP | 2006-087935 A | 4/2006 |
| JP | 2006-122723 A | 5/2006 |
| WO | 2004/096050 A1 | 11/2004 |

OTHER PUBLICATIONS

EP Communication, dated Jul. 27, 2009, issued in corresponding EP Application No. 09002457.1, 6 pages.

* cited by examiner

*Primary Examiner* — David Porta
*Assistant Examiner* — Marcus Taningco
(74) *Attorney, Agent, or Firm* — Sughrue Mion, PLLC

(57) ABSTRACT

A radiation image capturing system includes an image capturing apparatus for capturing a radiation image of a subject by irradiating the subject with a radiation emitted from a radiation source, a supply apparatus for supplying image capturing instruction information for capturing a plurality of radiation images of the subject, and a sorting apparatus for sorting the supplied image capturing instruction information into a predetermined processing order. The image capturing apparatus is controlled to capture the radiation images of the subject according to the processing order of the image capturing instruction information which has been sorted by the sorting apparatus.

19 Claims, 8 Drawing Sheets

RADIATION IMAGE CAPTURING SYSTEM, SORTING APPARATUS FOR SORTING IMAGE CAPTURING INSTRUCTION INFORMATION, PROGRAM AND RADIATION IMAGE CAPTURING METHOD

BACKGROUND OF THE INVENTION

1. Field of the Invention

The present invention relates to a radiation image capturing system and a radiation image capturing method for capturing a plurality of radiation images of a subject with image capturing apparatus, and also relates to a sorting apparatus for sorting image capturing instruction information for capturing a plurality of radiation images, into a processing order, and a program for being executed in the sorting apparatus.

2. Description of the Related Art

In the medical field, there have widely been used radiation image capturing apparatus which apply a radiation to a subject and guide the radiation that has passed through the subject to a radiation conversion panel, which captures a radiation image from the radiation.

One known radiation conversion panel is a stimulable phosphor panel which stores a radiation energy representative of radiation image information in a phosphor. When the stimulable phosphor panel is irradiated with stimulating light, the phosphor emits stimulated light representative of the stored radiation image information. The stimulable phosphor panel with the radiation image information recorded therein is supplied to a reading apparatus which reads the stored radiation image information as a visible radiation image.

In sites of medical practice such as operating rooms or the like, it is necessary to read recorded radiation image information immediately from a radiation conversion panel for the purpose of quickly and appropriately treating the patient. As a radiation conversion panel which meets such a requirement, there has been developed a radiation conversion panel having a solid-state imaging device for converting a radiation directly into an electric signal or converting a radiation into visible light with a scintillator and then converting the visible light into an electric signal to read a detected radiation image.

There are available in the art various image capturing apparatus of different specifications for capturing radiation images using radiation conversion panels depending on the conditions of patients as subjects to be imaged and image capturing conditions including body regions to be imaged. For example, Japanese Laid-Open Patent Publication No. 2001-340326 discloses a mixed system including an upstanding image capturing apparatus and a recumbent image capturing apparatus.

A radiation conversion panel which comprises a solid-state imaging device allows radiation image information recorded therein to be read therefrom immediately after it has captured the radiation image information. When a radiation image is captured by a stimulable phosphor panel, however, the stimulable phosphor panel needs to be supplied to a reading apparatus after the radiation image has been recorded in the stimulable phosphor panel and then the recorded radiation image is read from the stimulable phosphor panel by the reading apparatus. Therefore, it takes some time until the image reading process is completed after the radiation image has been captured. In particular, if the stimulable phosphor panel is housed in a cassette, then the stimulable phosphor panel has to be removed from the cassette and supplied to the reading apparatus and then delivered to a reader in the reading apparatus.

If a system which includes a reading apparatus for reading recorded radiation image information from a stimulable phosphor panel incorporates a plurality of image capturing apparatus, then the image reading process carried out by the reading apparatus needs to be controlled in rate, making the throughput of the system lower.

Certain medical diagnostic situations require that one patient be imaged to produce a plurality of radiation images including a frontal chest image, a lateral chest image, partial limb images, etc., and also that a plurality of radiation images be captured by a plurality of different image capturing apparatus. When the patient is required to change its imaging posture greatly, or when the patient is required to move between different image capturing apparatus, or when an image capturing apparatus is required to change its settings greatly between image capturing cycles, then the overall image capturing process tends to have its efficiency greatly lowered.

SUMMARY OF THE INVENTION

It is a general object of the present invention to efficiently capture a plurality of radiation images.

A major object of the present invention is to efficiently perform image capturing processes on a plurality of image capturing apparatus.

Another object of the present invention is to reduce a burden on a subject to be imaged.

A radiation image capturing system according to the present invention includes an image capturing apparatus for capturing a radiation image of a subject by irradiating the subject with a radiation emitted from a radiation source, a supply apparatus for supplying image capturing instruction information for capturing a plurality of radiation images of the subject, and a sorting apparatus for sorting the supplied image capturing instruction information into a predetermined processing order. The image capturing apparatus is controlled to capture the radiation images of the subject according to the processing order of the image capturing instruction information which has been sorted by the sorting apparatus.

Also, a sorting apparatus, according to the present invention, sorts image capturing instruction information when an image capturing apparatus and a supply apparatus are provided. The image capturing apparatus captures a radiation image of a subject by irradiating the subject with a radiation emitted from a radiation source, and the supply apparatus supplies image capturing instruction information for capturing a plurality of radiation images of the subject. The sorting apparatus sorts the image capturing instruction information supplied from the supply apparatus, into a predetermined processing order, and controls the image capturing apparatus to capture the radiation images of the subject according to the processing order of the sorted image capturing instruction information.

Further, a program, according to the present invention, is executed by a sorting apparatus to control an image capturing apparatus according to image capturing instruction information for capturing a plurality of radiation images of a subject. The image capturing apparatus captures each of the radiation images of the subject by irradiating the subject with a radiation emitted from a radiation source, and the image capturing instruction information is supplied by a supply apparatus. The program includes the steps of sorting the image capturing instruction information supplied from the supply apparatus, into a predetermined processing order, and controlling the image capturing apparatus to capture a plurality of radiation images of the subject according to the processing order of the sorted image capturing instruction information.

Still further, a radiation image capturing method, according to the present invention, is applied to a case where an image capturing apparatus for capturing a radiation image of a subject by irradiating the subject with a radiation emitted from a radiation source, and a supply apparatus for supplying image capturing instruction information for capturing a plurality of radiation images of the subject are provided. The method comprises the steps of sorting, by a sorting apparatus, the image capturing instruction information supplied from the supply apparatus, into a predetermined processing order, and controlling, by the sorting apparatus, the image capturing apparatus to capture the radiation images of the subject according to the processing order of the sorted image capturing instruction information.

According to the present invention, when instructions are given to capture a plurality of radiation images of the subject, the image capturing instruction information is sorted into a most efficient processing order, and the image capturing apparatus are controlled according to the processing order. Therefore, the radiation images can be captured efficiently by the image capturing apparatus.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
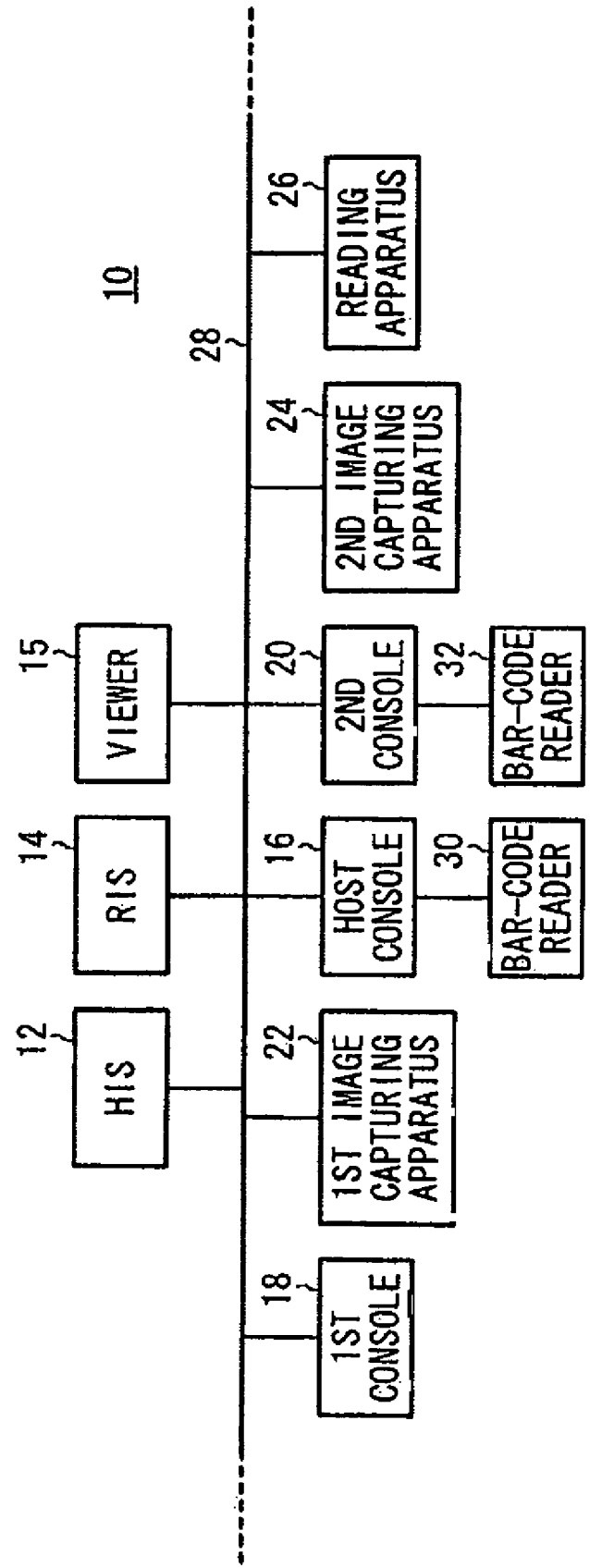
FIG. 1 is a block diagram of a radiation image capturing system according to an embodiment of the present invention.
Figure 2:
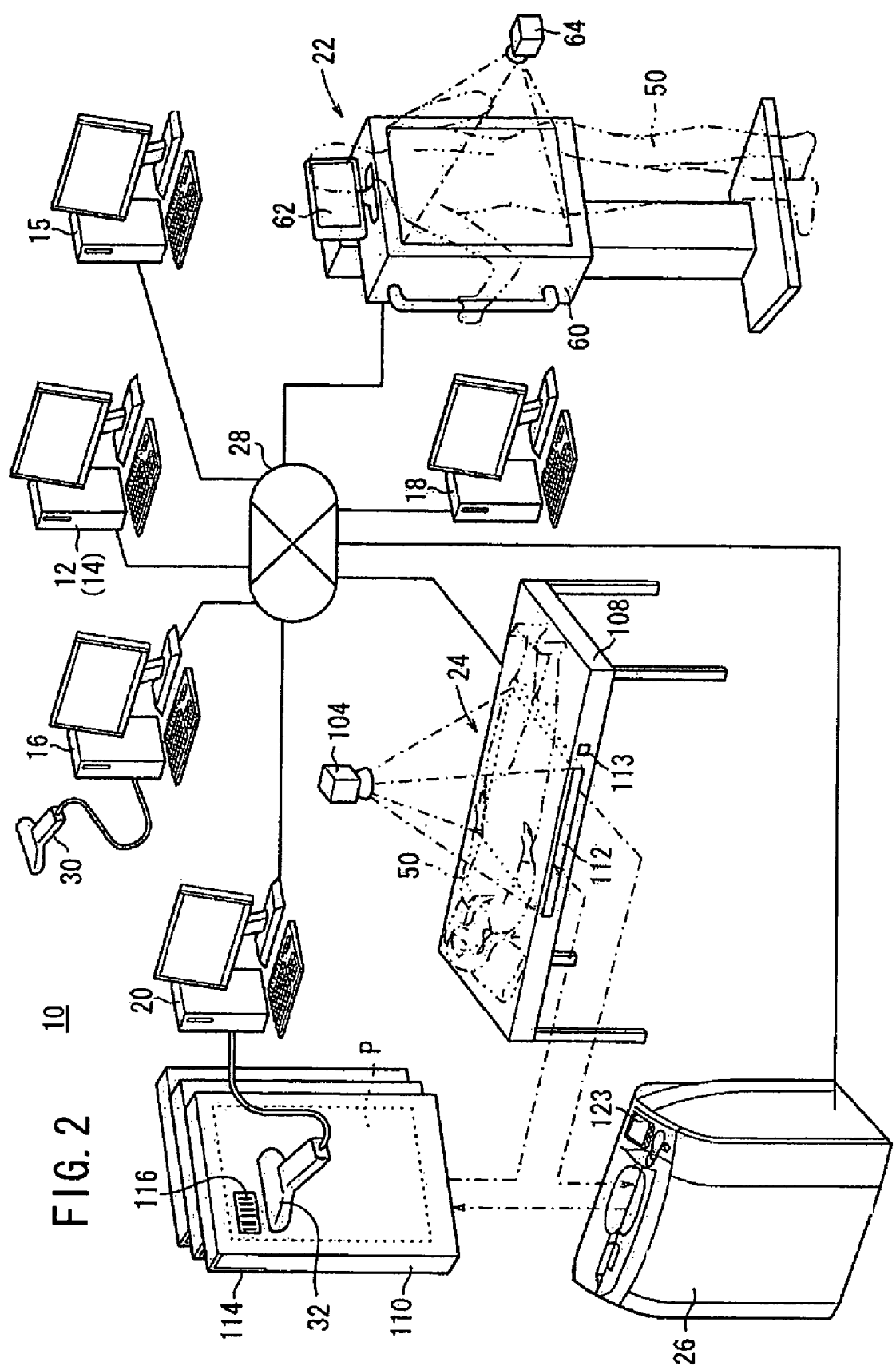
FIG. 2 is a schematic perspective view of the radiation image capturing system shown in FIG. 1.

FIGS. 1 and 2 show a configuration of a radiation image capturing system 10 according to an embodiment of the present invention. As shown in FIGS. 1 and 2, the radiation image capturing system 10 comprises a hospital information system (HIS) 12 for managing medical information processing (including medical coding) in a hospital, a radiology information system (RIS) (supply apparatus) 14 for managing radiation image capturing processes performed in the radiological department of the hospital under the management of the HIS 12, a viewer 15 for displaying radiation images to be interpreted by the doctor for diagnosis, a host console 16 placed in a control room near image capturing rooms in the radiological department, for managing various image capturing apparatus of different specifications by executing a program stored in an unillustrated memory, a first console 18 and a second console 20 placed in the control room for controlling particular image capturing apparatus, respectively, a first image capturing apparatus 22 for being controlled by the first console 18, a second image capturing apparatus 24 for being controlled by the second console 20, and a reading apparatus 26 for being controlled by the second console 20 to read radiation image information captured by the second image capturing apparatus 24. The above components of the radiation image capturing system 10 are interconnected by an in-house network 28 in the hospital. If necessary, other consoles, other image capturing apparatus, and components may also be connected to the in-house network 28.

The host console 16 acquires patient information such as the name, gender, age, etc. of a patient which has been set using the HIS 12, and image capturing instruction information such as a method of capturing a radiation image, a body region to be imaged, and an image capturing apparatus to be used to capture a radiation image, which has been set by the doctor or radiological technician using the RIS 14, and, if necessary, image capturing conditions such as a tube voltage, a tube current, an irradiation time, etc. to be set in the radiation source of the image capturing apparatus to be used, through the in-house network 28, and supplies the acquired information to the first console 18 or the second console 20. The host console 16 may be programmed to perform the processing sequence of the first console 18 or the second console 20. If the host console 16 is programmed to perform the processing sequence of the first console 18 or the second console 20, then since the first console 18 or the second console 20 may be dispensed with, the radiation image capturing system will become less costly. To the host console 16 and the second console 20, there are connected respective bar-code readers 30, 32 for acquiring ID information for identifying a radiation conversion panel, described later, to be used in the second image capturing apparatus 24.

Figure 3:
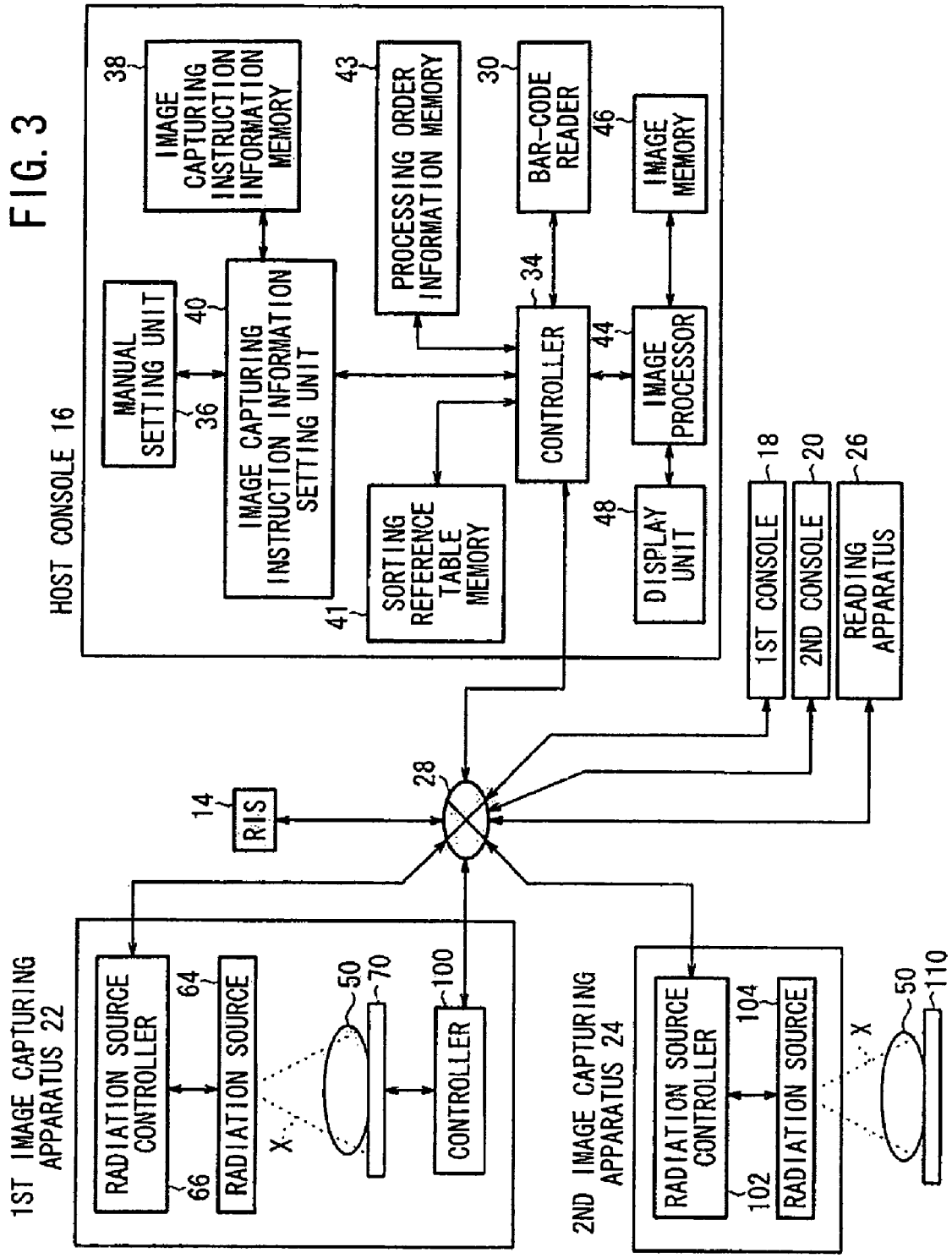
FIG. 3 is a block diagram of an assembly of a host console, a first image capturing apparatus and a second image capturing apparatus shown in FIG. 1.

FIG. 3 shows in block form an assembly of the host console 16, the first image capturing apparatus 22, and the second image capturing apparatus 24.

The host console 16 has a controller (sorting apparatus) 34 which, by executing the program, sends information to and receives information from the RIS 14, the first console 18, the second console 20, the first image capturing apparatus 22, the second image capturing apparatus 24, and the reading apparatus 26 through the in-house network 28, and sorts image capturing instruction information into a given processing order.

The host console 16 comprises a manual setting unit 36, an image capturing instruction information setting unit 40 for setting image capturing instruction information through the manual setting unit 36 or receiving image capturing instruction information set by the RIS 14 and storing the image capturing instruction information in an image capturing instruction information memory 38, an image processor 44 for processing radiation image information acquired from the first image capturing apparatus 22 or the second image capturing apparatus 24, an image memory 46 for storing the processed radiation image information, and a display unit 48 for displaying the radiation image information.

If a plurality of radiation images are to be captured using both the first image capturing apparatus 22 and the second image capturing apparatus 24, then the controller 34 sets a processing order for the first image capturing apparatus 22 and the second image capturing apparatus 24 for capturing radiation images according to image capturing instruction information, and supplies the image capturing instruction information to the first console 18 and the second console 20 according to the set processing order. At this time, the controller 34 sorts the image capturing instruction information using a sorting reference table stored in a sorting reference table memory 41, and stores the sorted image capturing instruction information as processing order information in a processing order information memory 43.

The first console 18 and the second console 20 have essentially the same functions as the host console 16 except for the controller 34 for acquiring image capturing instruction information from the RIS 14. The configurations of the host console 16, the first console 18, and the second console 20 may not necessarily be different from each other, but may be identical to each other.

The first image capturing apparatus 22 is an upstanding image capturing apparatus for capturing a radiation image of the chest or the like of a subject (patient) 50. The first image capturing apparatus 22 comprises a radiation source 64 for being controlled by a radiation source controller 66, an image capturing base 60 disposed in confronting relation to the radiation source 64, and a display unit 62 for displaying that the first image capturing apparatus 22 is being currently selected and information necessary for an image capturing process. The image capturing base 60 houses therein a radiation conversion panel which comprises a solid-state imaging device to be described later. The radiation source controller 66 controls the radiation source 64 according to image capturing conditions set by the host console 16.

Figure 4:
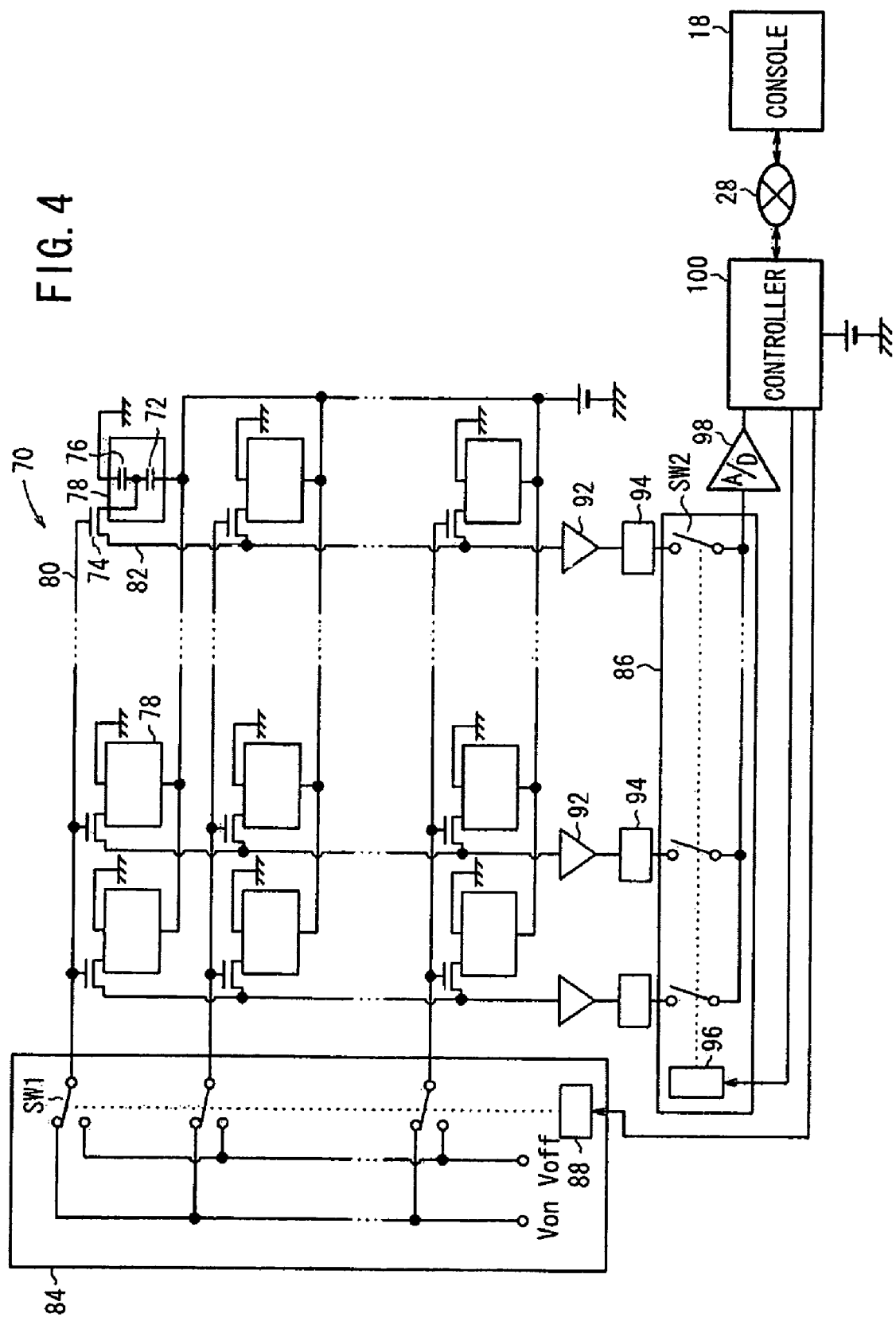
FIG. 4 is a block diagram of a circuit arrangement of a radiation conversion panel used in the radiation image capturing system.

FIG. 4 shows in block form a circuit arrangement of a radiation conversion panel 70 housed in the image capturing base 60.

The radiation conversion panel 70 comprises an array of thin-film transistors (TFTs) 74 arranged in rows and columns, a photoelectric conversion layer 72 made of a material such as amorphous selenium (a-Se) for generating electric charges upon detection of a radiation, the photoelectric conversion layer 72 being disposed over the array of TFTs 74, and an array of storage capacitors 76 connected to the photoelectric conversion layer 72. When the radiation is applied to the radiation conversion panel 70, the photoelectric conversion layer 72 generates electric charges, and the storage capacitors 76 store the generated electric charges. Then, the TFTs 74 are turned on along each row at a time to read the electric charges from the storage capacitors 76 as an image signal. In FIG. 4, the photoelectric conversion layer 72 and one of the storage capacitors 76 are shown as a pixel 78, and the pixel 78 is connected to one of the TFTs 74. Details of the other pixels 78 are omitted from illustration. Since amorphous selenium tends to change its structure and lose its function at high temperatures, it needs to be used within a certain temperature range. Therefore, some means for cooling the radiation conversion panel 70 should preferably be provided in the image capturing base 60.

The TFTs 74 connected to the respective pixels 78 are connected to respective gate lines 80 extending parallel to the rows and respective signal lines 82 extending parallel to the columns. The gate lines 80 are connected to a line scanning driver 84, and the signal lines 82 are connected to a multiplexer 86 serving as a reading circuit.

The gate lines 80 are supplied with control signals Von, Voff for turning on and off the TFTs 74 along the rows from the line scanning driver 84. The line scanning driver 84 comprises a plurality of switches SW1 for switching between the gate lines 80, and an address decoder 88 for outputting a selection signal for selecting one of the switches SW1 at a time. The address decoder 88 is supplied with an address signal from a controller 100.

The signal lines 82 are supplied with electric charges stored in the storage capacitors 76 of the pixels 78 through the TFTs 74 arranged in the columns. The electric charges supplied to the signal lines 82 are amplified by amplifiers 92 connected respectively to the signal lines 82. The amplifiers 92 are connected through respective sample and hold circuits 94 to the multiplexer 86. The multiplexer 86 comprises a plurality of switches SW2 for successively switching between the signal lines 82 and an address decoder 96 for outputting a selection signal for selecting one of the switches SW2 at a time. The address decoder 96 is supplied with an address signal from the controller 100. The multiplexer 86 has an output terminal connected to an A/D converter 98. A radiation image signal generated by the multiplexer 86 based on the electric charges from the sample and hold circuits 94 is converted by the A/D converter 98 into a digital image signal representing radiation image information, which is supplied to the controller 100. The controller 100 supplies the acquired radiation image information through the in-house network 28 to the first console 18 which controls the first image capturing apparatus 22.

The TFTs 74 functioning as switching devices may be combined with other imaging devices such as a CMOS (Complementary Metal-Oxide Semiconductor) image sensor. Alternatively, a CCD (Charge-Coupled Device) image sensor which transfers electric charges while shifting them with shift pulses corresponding to the gate signals for the TFTs may be used.

The second image capturing apparatus 24 is a recumbent image capturing apparatus for capturing a radiation image of a wide area including the chest of the subject 50. The second image capturing apparatus 24 comprises a radiation source 104 for being controlled by a radiation source controller 102 and an image capturing base 108 disposed in confronting relation to the radiation source 104. The image capturing base 108 has a slot 112, defined in a side wall thereof, through which a cassette 110 housing a stimulable phosphor panel P therein can be loaded into the image capturing base 108. The image capturing base 108 has a display unit 113 disposed on a side wall thereof near the slot 112 for displaying that the second image capturing apparatus 24 is being currently selected. The second image capturing apparatus 24 is controlled by the second console 20 through the in-house network 28. The second image capturing apparatus 24 has different specifications from the first image capturing apparatus 22. The radiation source controller 102 controls the radiation source 104 according to image capturing conditions set by the host console 16.

The stimulable phosphor panel P comprises a support body and a stimulable phosphor layer disposed on the support body. The stimulable phosphor layer stores the energy of a radiation X that is applied thereto. When the stimulable phosphor layer is irradiated with stimulating light, it emits stimulated light depending on the stored energy. When the stimulable phosphor layer is irradiated with erasing light, it discharges any remaining energy stored therein and can be reused.

The stimulable phosphor panel P housed in the cassette 110 is removable from the cassette 110 when a lid member 114 on the cassette 110 is opened. A bar code 116 which records therein identification information including an identification number for identifying the stimulable phosphor panel P housed in the cassette 110, the size of the stimulable phosphor panel P, the sensitivity of the stimulable phosphor panel P, etc. is applied to an outer surface of the cassette 110. The bar code 116 can be read by the bar-code reader 32 connected to the second console 20 or the bar-code reader 30 connected to the host console 16.

Figure 5:
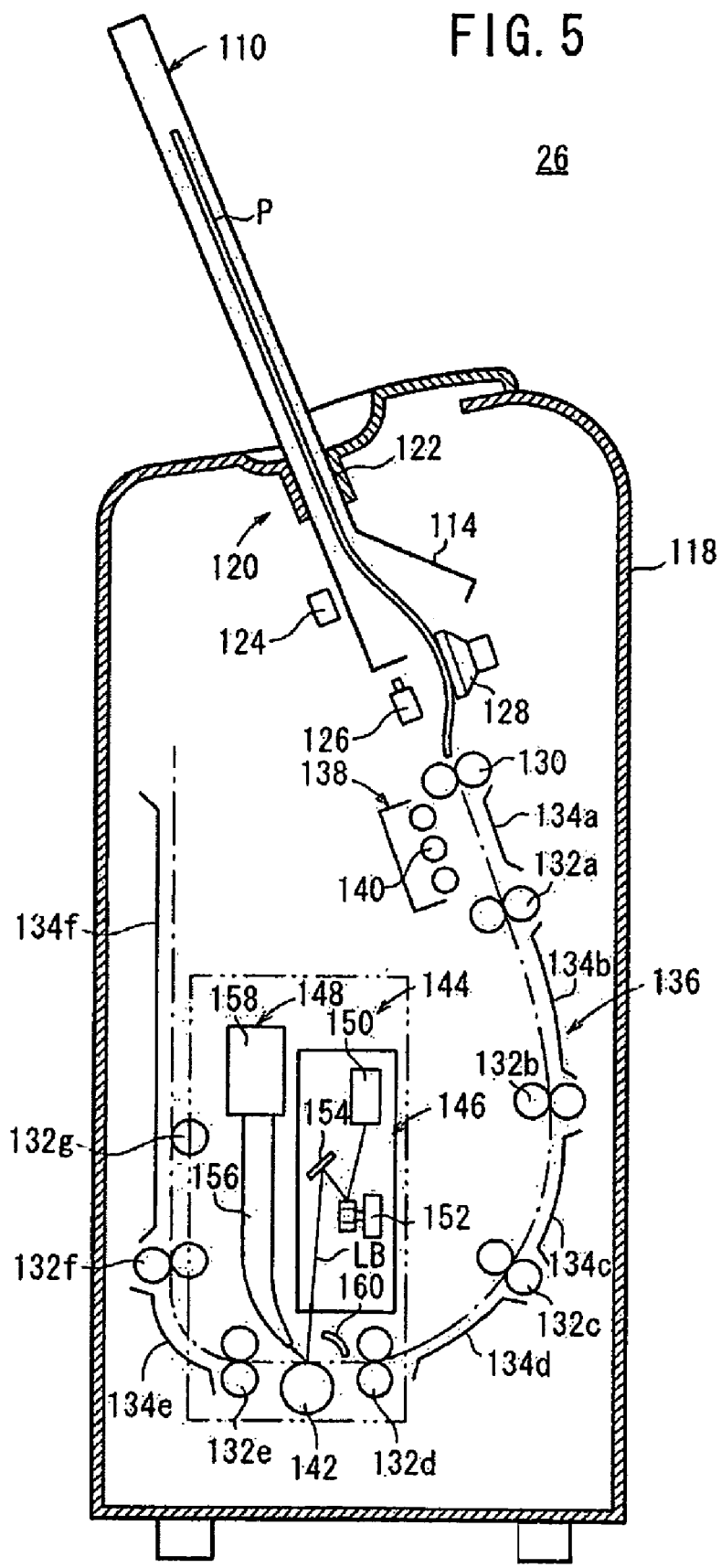
FIG. 5 is a vertical cross-sectional view of a reading apparatus of the radiation image capturing system.

Radiation image information that has been recorded in the stimulable phosphor panel P is read by the reading apparatus 26 which is constructed as shown in FIG. 5. The reading apparatus 26 as well as the second image capturing apparatus 24 is controlled by the second console 20 through the in-house network 28.

As shown in FIG. 5, the reading apparatus 26 has a cassette loader 120 disposed in an upper portion of a casing 118 and a display unit 123 (see FIG. 2) disposed on the upper portion of the casing 118 for displaying that the reading apparatus is being currently selected and information required for a reading process. The cassette loader 120 has a loading slot 122 for receiving therein the cassette 110 which houses therein the stimulable phosphor panel P with recorded radiation image information. The casing 118 of the reading apparatus 26 accommodates therein, near the loading slot 122, a bar-code reader 124 for reading the identification information recorded in the bar code 116 on the cassette 110, an unlock mechanism 126 for unlocking the lid member 114 of the cassette 110, a suction cup 128 for attracting and removing the stimulable phosphor panel P from the cassette 110 at the time the lid member 114 is opened, and a pair of nip rollers 130 for gripping and feeding the stimulable phosphor panel P removed by the suction cup 128.

The nip rollers 130 are followed by a plurality of feed rollers 132*a* through 132*g* and a plurality of guide plates 134*a* through 134*f* which jointly make up a curved feed path 136. The curved feed path 136 extends downwardly from the cassette loader 120, then extends substantially horizontally at its lowermost portion, and then extends substantially vertically upwardly. The curved feed path 136 thus shaped is effective to make the reading apparatus 26 small in size.

Between the nip rollers 130 and the feed rollers 132*a*, there is disposed an erasing unit 138 for erasing radiation image information remaining in the stimulable phosphor panel P from which desired radiation image information has been read. The erasing unit 138 has a plurality of erasing light sources 140 such as cold cathode tubes or the like for emitting erasing light.

A platen roller 142 is disposed between the feed rollers 132*d*, 132*e* which are positioned in the lowermost portion of the curved feed path 136. The platen roller 142 is disposed beneath a scanning unit 144 for reading the desired radiation image information recorded in the stimulable phosphor panel P.

The scanning unit 144 comprises a stimulator 146 for emitting a laser beam LB as stimulating light to scan the stimulable phosphor panel P and a reader 148 for reading stimulated light emitted from the stimulable phosphor panel P which is stimulated by the laser beam LB, the stimulated light being representative of the radiation image information.

The stimulator 146 comprises a laser oscillator 150 for outputting the laser beam LB, a rotary polygon mirror 152 for deflecting the laser beam LB in a main scanning direction across the stimulable phosphor panel P, and a reflecting mirror 154 for reflecting the laser beam LB to the stimulable phosphor panel P as it passes over the platen roller 142.

The reader 148 comprises a light guide 156 having a lower end disposed near the stimulable phosphor panel P over the platen roller 142, and a photomultiplier 158 connected to an upper end of the light guide 156 for converting the stimulated light from the stimulable phosphor panel P into an electric signal which represents the radiation image information stored in the stimulable phosphor panel P. A light collecting mirror 160 for collecting the stimulated light from the stimulable phosphor panel P is disposed near the lower end of the light guide 156. The photomultiplier 158 supplies the electric signal representing the radiation image information to the second console 20 through the in-house network 28.

Image capturing apparatus of other specifications, such as a CT apparatus, an MR apparatus, etc. may be connected to the in-house network 28, and consoles (processors) for controlling these image capturing apparatus may also be connected to the in-house network 28.

Figure 7:
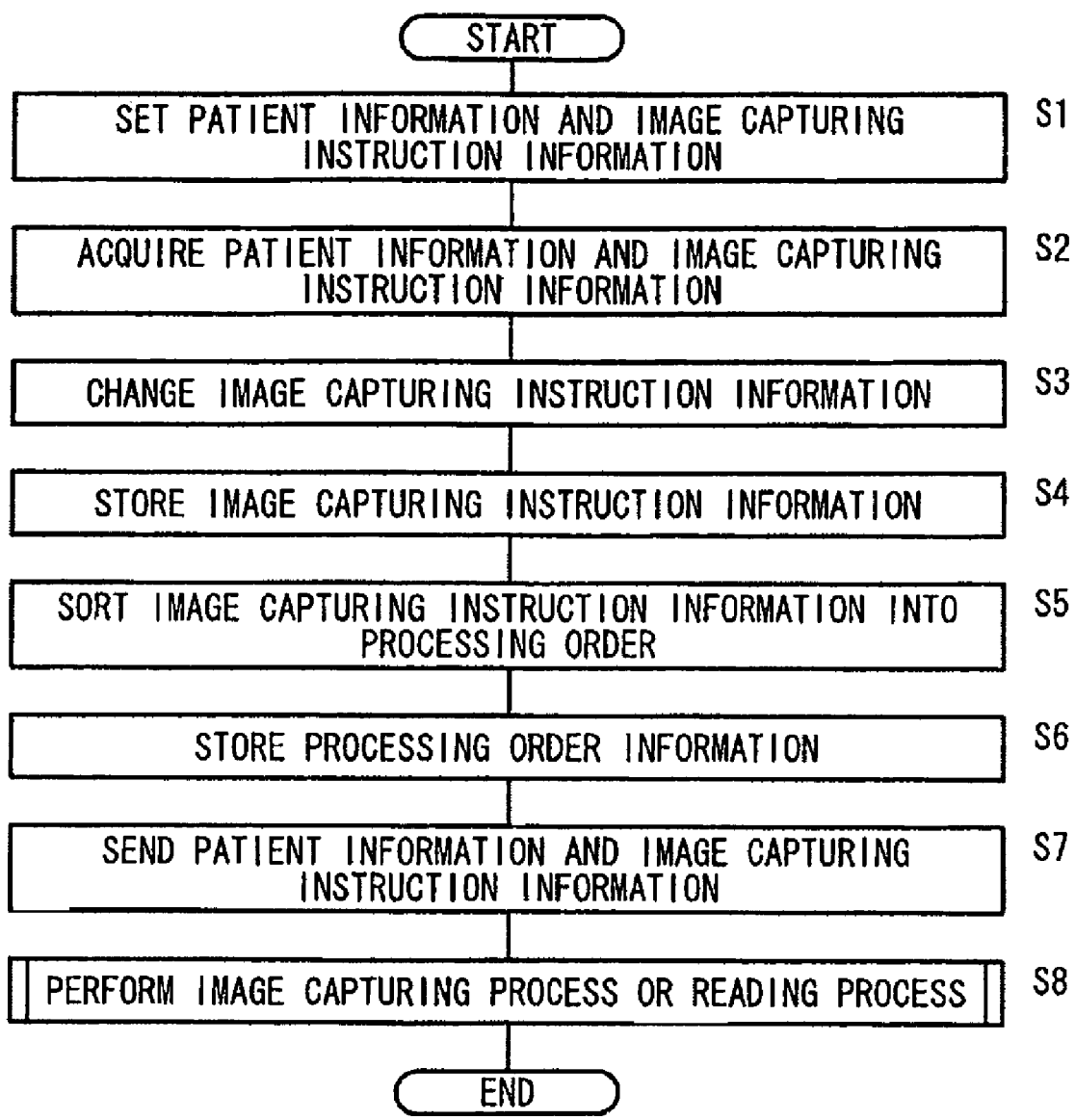
FIG. 7 is a flowchart of an operating sequence of the system shown in FIG. 1.
Figure 8:
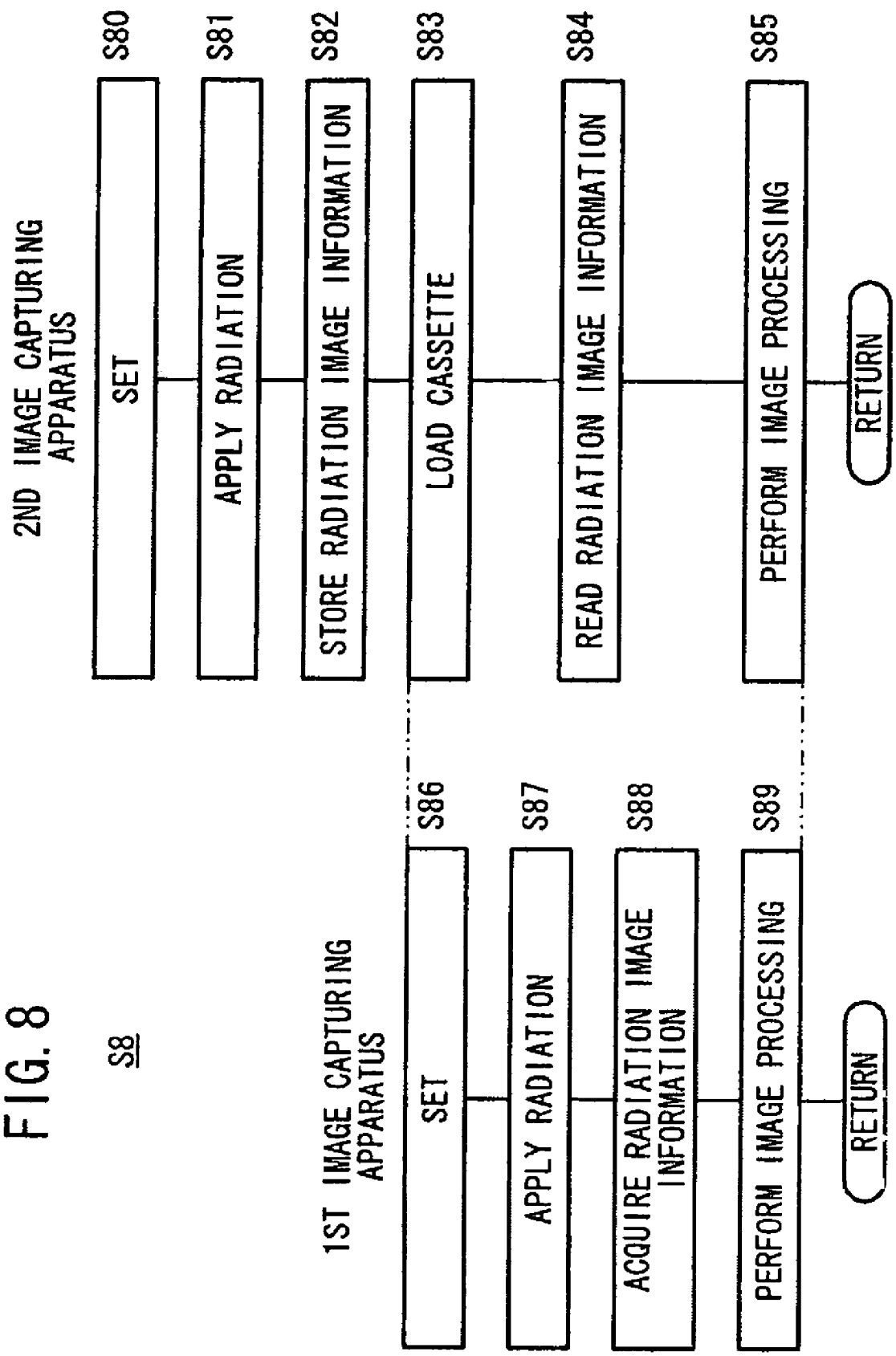
FIG. 8 is a flowchart of step S8 in FIG. 7.

The radiation image capturing system 10 according to the present invention is basically constructed as described above. Operation (radiation image capturing method) of the radiation image capturing system 10 will be described below with reference to flowcharts in FIGS. 7 and 8.

First, patient information such as the name, gender, age, etc. of a patient is set using the HIS 12, and image capturing instruction information such as a method of capturing a radiation image, a body region to be imaged, and an image capturing apparatus to be used to capture a radiation image, is set in relation to the patient information using the RIS 14 (step S1).

The controller 34 of the host console 16 that is installed in the radiological department acquires the patient information and the image capturing instruction information from the RIS 14 via the in-house network 28 (step 2). The radiological technician sets and changes the image capturing instruction information using the manual setting unit 36 of the host console 16 (step 3).

For example, the radiological technician sets image capturing conditions including a tube voltage, a tube current, an irradiation time, etc. depending on the body region to be imaged of the subject 50, with respect to the radiation source of the image capturing apparatus that is set in the acquired image capturing instruction information. Also, the radiological technician may set these image capturing conditions using the RIS 14.

It is assumed that the doctor selects the first image capturing apparatus 22 using the RIS 14, but the subject 50 is using a wheelchair and cannot be imaged by the first image capturing apparatus 22. In this case, the doctor places the cassette 110 between the wheelchair and the subject 50, and changes the image capturing instruction information about the image capturing apparatus in order to switch to an image capturing process using the radiation source 104 of the second image capturing apparatus 24. On the other hand, if the second image capturing apparatus 24 which is selected by the doctor cannot be used because it is being in an adjustment process, for example, then the doctor changes the image capturing instruction information from an image capturing process using the second image capturing apparatus 24 to an image capturing process using the first image capturing apparatus 22 in order to switch to the image capturing process using the first image capturing apparatus 22 as an alternative.

The image capturing instruction information setting unit 40 temporarily stores the patient information and the image capturing instruction information which have been acquired or the image capturing instruction information including changed or newly set image capturing conditions into the image capturing instruction information memory 38 (step S4).

By executing a program stored in an unillustrated memory, the controller 34 sorts a plurality of items of image capturing instruction information read from the image capturing instruction information memory 38 via the image capturing instruction information setting unit 40, into a processing order for a most efficient image capturing process, using the sorting reference table stored in the sorting reference table memory 41 (step S5).

Figure 6:
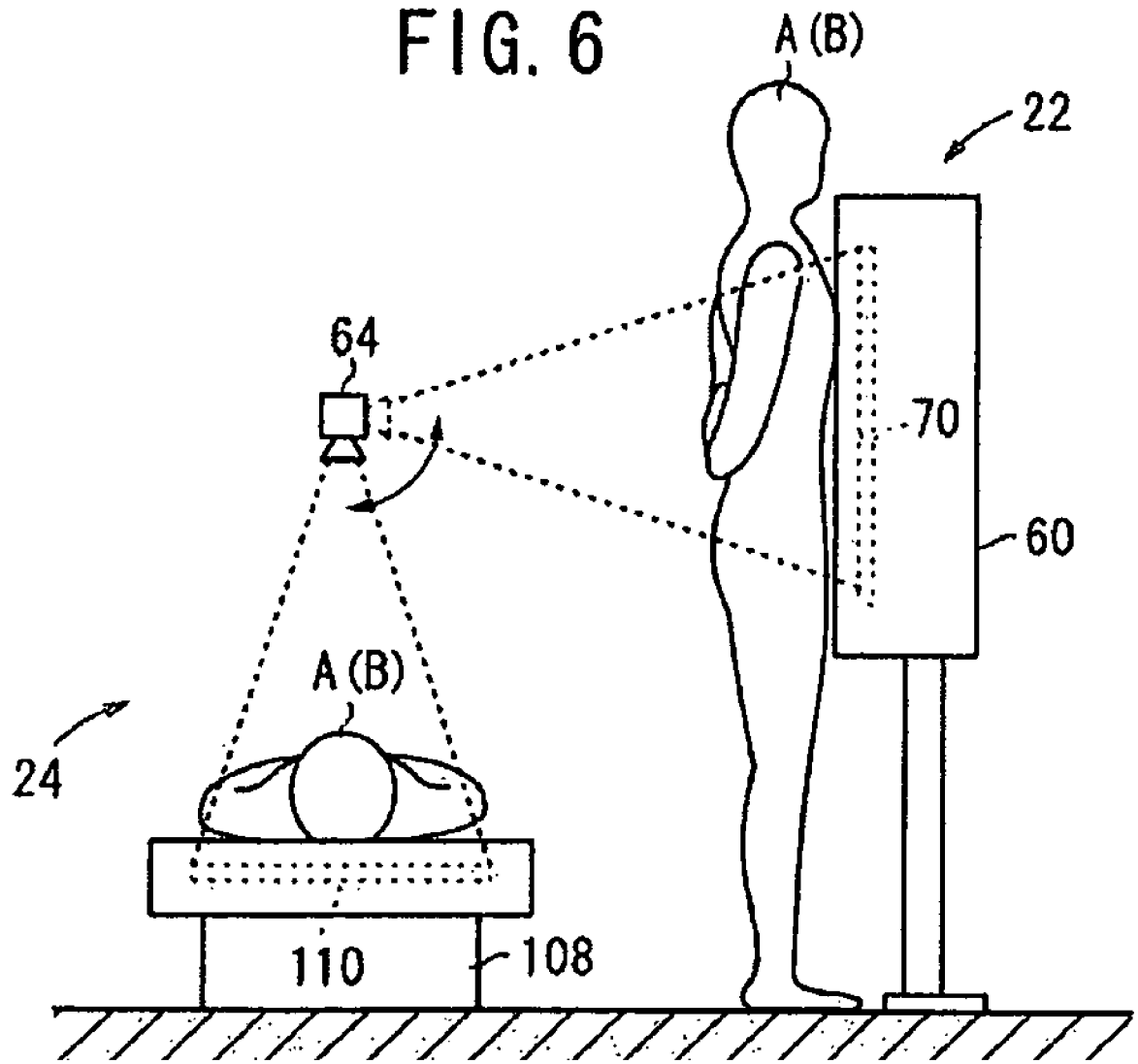
FIG. 6 is a diagram showing an image capturing procedure using the first image capturing apparatus and the second image capturing apparatus.

For example, it is assumed that the image capturing instruction information represents an image capturing procedure for capturing radiation images of a plurality of body regions to be imaged A, B with the first image capturing apparatus 22 and the second image capturing apparatus 24, and the radiation source 64 is shared by the first image capturing apparatus 22 and the second image capturing apparatus 24, as shown in FIG. 6. The processing order according to the image capturing instruction information represents (1) an image capturing process which uses the first image capturing apparatus 22 for the body region A, to (2) an image capturing process which uses the second image capturing apparatus 24 for the body region A, to (3) an image capturing process which uses the first image capturing apparatus 22 for the body region B, to (4) an image capturing process which uses the second image capturing apparatus 24 for the body region B. The controller 34 sorts these image capturing processes into a new processing order representing the image capturing process (1) to the image capturing process (2) to the image capturing process (4) to the image capturing process (3), and stores processing order information representative of the new processing order into the processing order information memory 43 (step S6).

According to the new processing order, when the image capturing process (2) switches to the image capturing process (4), the radiation source 64 may remain oriented toward the image capturing base 108 of the second image capturing apparatus 24, and hence does not need to be positionally adjusted. When the image capturing process (4) switches to the image capturing process (3), the image capturing process can be performed by the first image capturing apparatus 22 concurrently with a reading process, to be described later, carried out by the reading apparatus 26 for reading the radiation image information recorded in the stimulable phosphor panel P housed in the cassette 110 by the second image capturing apparatus 24. As a consequence, the radiation image capturing system 10 can efficiently acquire a plurality of radiation images.

If the processing order according to the image capturing instruction information for the subject 50 is set to represent (1) an image capturing process for capturing a frontal chest image, to (2) an image capturing process for capturing a right hand image, to (3) an image capturing process for capturing a lateral chest image, then the subject 50 is required to lie face up on the image capturing base 108 of the second image capturing apparatus 24 for the second image capturing apparatus 24 to capture a frontal chest image, then to rise and put the right hand on the image capturing base 108 for the second image capturing apparatus 24 to capture a right hand image, and thereafter to lie on its side on the image capturing base 108 for the second image capturing apparatus 24 to capture a lateral chest image. The controller 34 sorts these image capturing processes into a new processing order representing the image capturing process (1), to the image capturing process (3), to the image capturing process (2), and stores processing order information representative of the new processing order into the processing order information memory 43 (step S6).

According to the new processing order, the subject 50 may remain lying on the image capturing base 108 while the image capturing process (1) and the image capturing process (3) are being successively carried out, and then rise for the image capturing process (2). In the image capturing processes (1), (3), the subject 50 is irradiated with the radiation X emitted from the radiation source 104 in substantially the same irradiation range. Consequently, it is not necessary to adjust the irradiation range for the subject 50 when the image capturing process (1) changes to the image capturing process (3).

According to the processing order information stored in the processing order information memory 43, the controller 34 reads the patient information and the image capturing instruction information from the image capturing instruction information memory 38, and sends the patient information and the image capturing instruction information to the first console 18, the second console 20, or the reading apparatus 26 (step S7). After having confirmed the completion of the sending of the image capturing instruction information, the controller 34 deletes the image capturing instruction information from the image capturing instruction information memory 38. If the host console 16 serves as a processor capable of performing processing sequences for a plurality of image capturing apparatus of different specifications, then the host console 16 may be selected as a console, instead of the first console 18 or the second console 20, for performing a processing sequence for the first image capturing apparatus 22 or the second image capturing apparatus 24.

The console to which the patient information and the image capturing instruction information have been sent now performs a process of capturing radiation image using the image capturing apparatus under its control or a reading process, according to the image capturing instruction information (step S8).

First, a process of capturing radiation image information of the subject 50 with the second image capturing apparatus 24 controlled by the second console 20 will be described below. When the second image capturing apparatus 24 is selected, the display unit 113 on a side portion of the image capturing base 108 displays that the second image capturing apparatus 24 is being selected, prompting the radiological technician to guide the subject 50 to the second image capturing apparatus 24 for an image capturing process.

When the second console 20 receives the image capturing instruction information from the host console 16, the second console 20 sets, in step S80, a tube voltage, a tube current, and an irradiation time, i.e., image capturing conditions included in the image capturing instruction information, in the radiation source controller 102 of the second image capturing apparatus 24.

The radiological technician uses the bar-code reader 32 connected to the second console 20 to read the bar code 116 attached to the cassette 110, thereby acquiring identification information including an identification number for identifying the stimulable phosphor panel P housed in the cassette 110, the size of the stimulable phosphor panel P, the sensitivity of the stimulable phosphor panel P, etc.

After having loaded the cassette 110 into the slot 112 of the second image capturing apparatus 24, the radiological technician operates an image capturing switch, not shown, to start an image capturing process. The radiation source controller 102 controls the radiation source 104 according to the set image capturing conditions to apply the radiation X to the subject 50 (step S81). The radiation x that has passed through the subject 50 is applied to the stimulable phosphor panel P housed in the cassette 110. As a result, radiation image information of the subject 50 is recorded in the stimulable phosphor panel P (step S82).

The radiological technician then removes the cassette 110 housing therein the stimulable phosphor panel P with the recorded radiation image information, from the second image capturing apparatus 24, and thereafter loads the cassette 110 into the cassette loader 120 of the reading apparatus 26 (step S83). The radiological technician can reliably recognize that the reading process is to be carried out by the reading apparatus 26, by seeing the display unit 123 on the cassette loader 120 which displays that the reading apparatus 26 is selected.

When the cassette 110 is loaded into the cassette loader 120, the bar-code reader 124 in the cassette loader 120 reads the bar code 116 attached to the cassette 110 to acquire the identification information including the identification number, the size, the sensitivity, etc. of the stimulable phosphor panel P. The acquired identification information is compared with the identification information read by the bar-code reader 32 connected to the second console 20 to confirm the correspondence between the subject 50 and the radiation image information.

After the identification information is read, the unlock mechanism 126 is actuated to unlock and open the lid member 114. The suction cup 128 attracts the stimulable phosphor panel P, removes the stimulable phosphor panel P out of the cassette 110, and feeds the stimulable phosphor panel P between the nip rollers 130. The stimulable phosphor panel P which is gripped by the nip rollers 130 is then fed to a position beneath the scanning unit 144 through the curved feed path 136 made up of the feed rollers 132a through 132g and the guide plates 134a through 134f.

Beneath the scanning unit 144, the stimulable phosphor panel P is fed substantially horizontally in an auxiliary scanning direction by the feed rollers 132d, 132e. At the same time, the laser beam LB output from the laser oscillator 150 of the stimulator 146 is reflected and deflected by the polygon mirror 152 that is rotating at a high speed, and then guided by the reflecting mirror 154 to the stimulable phosphor panel P whose lower surface is supported by the platen roller 142, thereby scanning the stimulable phosphor panel P in a main scanning direction.

By being irradiated with the laser beam LB, the stimulable phosphor panel P is stimulated to emit stimulated light representative of the radiation image information recorded therein. The stimulated light is applied directly or via the light collecting mirror 160 to the lower end of the light guide 156 which is disposed near the stimulable phosphor panel P and extends in the main scanning direction. The stimulated light which has entered the light guide 156 is repeatedly reflected in the light guide 156 and guided to the photomultiplier 158. The photomultiplier 158 converts the stimulated light into an electric signal representative of the radiation image information recorded in the stimulable phosphor panel P. In this manner, the radiation image information recorded in the stimulable phosphor panel P is read by the scanning unit 144 of the reading apparatus 26 (step S84).

The radiation image information thus read by the scanning unit 144 is transmitted to the second console 20 through the in-house network 28. The second console 20 processes the received radiation image information depending on the specifications of the second image capturing apparatus 24 (step S85). Then, the second console 20 displays a radiation image based on the processed radiation image information for the radiological technician to confirm the radiation image, and then transmits the radiation image information to the viewer 15 through the in-house network 28. The doctor then interprets for diagnosis a radiation image that is displayed by the viewer 15 based on the radiation image information. If the second console 20 is processing other radiation image information that has already been received thereby, then the controller 34 of the host console 16 searches for another processor capable of performing its processing sequence, and sends the radiation image information acquired from the second image capturing apparatus 24, to the retrieved other processor to process the radiation image information.

While the radiation image information recorded in the stimulable phosphor panel P is being read by the reading apparatus 26, an image capturing process is carried out by the first image capturing apparatus 22. A process of capturing radiation image information of the subject 50 with the first image capturing apparatus 22 controlled by the first console 18 will be described below. When the first image capturing apparatus 22 is selected, the display unit 62 on the image capturing base 60 displays that the first image capturing apparatus 22 is selected, prompting the radiological technician to guide the subject 50 to the first image capturing apparatus 22 for an image capturing process.

When the first console 18 receives the image capturing instruction information from the host console 16, the first console 18 sets a tube voltage, a tube current, and an irradiation time, i.e., image capturing conditions included in the image capturing instruction information, in the radiation source controller 66 of the first image capturing apparatus 22 (step S86).

After having positioned the subject 50 in a given position on the image capturing base 60, the radiological technician operates an image capturing switch, not shown, to start an image capturing process. The radiation source controller 66 controls the radiation source 64 according to the set image capturing conditions to apply the radiation X to the subject 50 (step S87). The radiation X that has passed through the subject 50 is applied to the radiation conversion panel 70.

The radiation X is converted into electric signals by the photoelectric conversion layer 72 of the pixels 78 of the radiation conversion panel 70 (FIG. 4). The electric signals are stored as electric charges in the storage capacitors 76. The stored electric charges, which represent radiation image information of the subject 50, are read from the storage capacitors 76 according to address signals which are supplied from the controller 100 to the line scanning driver 84 and the multiplexer 86.

Specifically, in response to the address signal supplied from the controller 100, the address decoder 88 of the line scanning driver 84 outputs a selection signal so as to select one of the switches SW1, which supplies the control signal Von to the gates of the TFTs 74 connected to the gate line 80 corresponding to the selected switch SW1. In response to the address signal supplied from the controller 100, the address decoder 96 of the multiplexer 86 outputs a selection signal, which operates to successively turn on the switches SW2 so as to switch between the signal lines 82, for thereby reading the electric charges stored in the storage capacitors 76 of the pixels 78 connected to the selected gate line 80, through the signal lines 82.

The electric charges (radiation image information) read from the storage capacitors 76 of the pixels 78 connected to the selected gate line 80 are amplified by the respective amplifiers 92, sampled by the sample and hold circuits 94, and supplied to the multiplexer 86. Based on the supplied electric charges, the multiplexer 86 generates and supplies a radiation image signal to the A/D converter 98, which converts the radiation image signal into a digital signal. The digital signal which represents the radiation image information is transmitted from the controller 100 to the first console 18 through the in-house network 28 (step S88).

Similarly, the address decoder 88 of the line scanning driver 84 successively turns on the switches SW1 to switch between the gate lines 80 according to the address signal supplied from the controller 100. The electric charges stored in the storage capacitors 76 of the pixels 78 connected to the successively selected gate lines 80 are read through the signal lines 82, and processed by the multiplexer 86 and the A/D converter 98 into digital signals, which are transmitted from the controller 100 to the first console 18 through the in-house network 28 (step S88).

The first console 18 processes the radiation image information represented by the received digital signals depending on the specifications of the first image capturing apparatus 22 (step S89). Then, the first console 18 displays a radiation image based on the processed radiation image information for the radiological technician to confirm the radiation image, and then transmits the radiation image information to the viewer 15 through the in-house network 28. The doctor then interprets for diagnosis a radiation image that is displayed by the viewer 15 based on the radiation image information. If the first console 18 is processing other radiation image information that has already been received thereby, then the controller 34 of the host console 16 searches for another processor capable of performing its processing sequence, and sends the radiation image information acquired from the first image capturing apparatus 22 to the retrieved other processor to process the radiation image information.

The present invention is not limited to the illustrated embodiment. Rather, changes and modifications may be made to the embodiment without departing from the scope of the invention.

For example, that the first image capturing apparatus 22, the second image capturing apparatus 24, or the reading apparatus 26 is selected may be displayed on the display unit of the first console 18 or the second console 20, instead of the display unit 113, 62, or 123.

In the illustrated embodiment, the radiation conversion panel 70 which comprises the solid-state imaging device shown in FIG. 4 is incorporated in the first image capturing apparatus 22, and the stimulable phosphor panel P is loaded in the second image capturing apparatus 24. However, the stimulable phosphor panel P and a reader for reading radiation image information recorded in the stimulable phosphor panel P may be incorporated in the first image capturing apparatus 22. In this case, after radiation image information is captured by the second image capturing apparatus 24, it is read by the reading apparatus 26. At the same time, radiation image information can be captured and read by the first image capturing apparatus 22. Accordingly, radiation image information can efficiently be acquired.

The radiation conversion panel 70 which comprises the solid-state imaging device may be applied to the second image capturing apparatus 24. In this case, after radiation image information is captured by the second image capturing apparatus 24, it is read from the radiation conversion panel 70. At the same time, radiation image information can be captured by the first image capturing apparatus 22. Accordingly, radiation image information can efficiently be acquired.

Also, for example, the radiation conversion panel 70 is a direct-conversion radiation detector which directly converts the dose of the applied radiation X into an electric signal with the photoelectric conversion layer 72. Instead of the direct-conversion radiation detector, the present invention may employ an indirect-conversion radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the present invention may employ a light readout type of radiation detector for acquiring radiation image information. The light readout type of radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices, which generate an electric current, and the electric current is acquired as radiation image information. When erasing light is applied to the radiation detector, radiation image information representing a residual electrostatic latent image is erased from the radiation detector, which can thus be reused (see Japanese Laid-Open Patent Publication No. 2000-105297).

In the above embodiment, the doctor sets patient information using the HIS 12, and the doctor or the radiological technician sets image capturing instruction information using the RIS 14. The information is supplied to the host console 16 via the in-house network 28, and then supplied from the host console 16 to the first console 18 or the second console 20. Instead of the above, the doctor or the radiological technician may set patient information and image capturing instruction information directly on the host console 16, the first console 18, or the second console 20. Alternatively, the doctor or the radiological technician may set patient information and image capturing instruction information using the HIS 12 or the RIS 14.

What is claimed is:

1. A radiation image capturing system comprising:
    an image capturing apparatus for capturing a radiation image of a subject by irradiating the subject with a radiation emitted from a radiation source;
    a supply apparatus for supplying image capturing instruction information for capturing a plurality of radiation images of the subject; and
    a sorting apparatus for sorting the supplied image capturing instruction information into a predetermined processing order;
    wherein the image capturing apparatus is controlled to capture the radiation images of the subject according to the processing order of the image capturing instruction information which has been sorted by the sorting apparatus; and
    wherein the sorting apparatus receives the instruction information for capturing the plurality of radiation images as a plurality of instructions in a first sequence and sorts the plurality of instructions into the predetermined processing order, said predetermined processing order being different than the first sequence.

2. A radiation image capturing system according to claim 1, wherein the image capturing apparatus comprises:
    a first image capturing apparatus for recording radiation image information in a first radiation conversion panel incorporated in the first image capturing apparatus by irradiating the first radiation conversion panel with the radiation through the subject;
    a second image capturing apparatus for recording radiation image information in a second radiation conversion panel by irradiating the second radiation conversion panel with the radiation through the subject, and reading the radiation image information from the second radiation conversion panel; and
    a reading apparatus which is loaded with the second radiation conversion panel, for reading the radiation image information recorded in the second radiation conversion panel;
    wherein the sorting apparatus sets the processing order such that after an image capturing process of the second image capturing apparatus is carried out, an image capturing process of the first image capturing apparatus and a reading process of the reading apparatus are carried out concurrently with each other.

3. A radiation image capturing system according to claim 2, wherein the first image capturing apparatus, the second image capturing apparatus, and the reading apparatus have respective display units for displaying the processing order set by the sorting apparatus.

4. A radiation image capturing system according to claim 1, wherein the image capturing apparatus comprises a plurality of image capturing apparatus of different specifications, and the sorting apparatus sorts the image capturing instruction information into a processing order so as to minimize a period of time required by image capturing processes carried out by the image capturing apparatus of different specifications.

5. A radiation image capturing system according to claim 4, wherein the image capturing apparatus of different specifications have respective display units for displaying the processing order set by the sorting apparatus.

6. A radiation image capturing system according to claim 1, wherein the sorting apparatus sorts the image capturing instruction information into a processing order so as to minimize a period of time required to change an imaging posture of the subject for the image capturing apparatus.

7. The radiation image capturing system of claim 1, wherein the sorting apparatus receives the instruction information for capturing the plurality of radiation images as a plurality of instructions, and the predetermined processing order comprises a temporal sequence for the plurality of instructions taking into account at least one of: body part images being captured and an amount of movement of imaging equipment to obtain the radiation images of the body parts to provide efficient sequence of image capturing.

8. A sorting apparatus for sorting image capturing instruction information when an image capturing apparatus and a supply apparatus are provided, the image capturing apparatus capturing a radiation image of a subject by irradiating the subject with a radiation emitted from a radiation source, and the supply apparatus supplying image capturing instruction information for capturing a plurality of radiation images of the subject,
wherein the sorting apparatus sorts the image capturing instruction information supplied from the supply apparatus, into a predetermined processing order, and controls the image capturing apparatus to capture the radiation images of the subject according to the processing order of the sorted image capturing instruction information; and
wherein the sorting apparatus receives the instruction information for capturing the plurality of radiation images as a plurality of instructions in a first sequence and sorts the plurality of instructions into the predetermined processing order, said predetermined processing order being different than the first sequence.

9. A sorting apparatus according to claim 8, wherein the image capturing apparatus comprises:
a first image capturing apparatus for recording radiation image information in a first radiation conversion panel incorporated in the first image capturing apparatus by irradiating the first radiation conversion panel with the radiation through the subject; and
a second image capturing apparatus for recording radiation image information in a second radiation conversion panel by irradiating the second radiation conversion panel with the radiation through the subject, and reading the radiation image information from the second radiation conversion panel; and
wherein when a reading apparatus which is loaded with the second radiation conversion panel is further provided, for reading the radiation image information recorded in the second radiation conversion panel, the sorting apparatus sets the processing order such that after an image capturing process of the second image capturing apparatus is carried out, an image capturing process of the first image capturing apparatus and a reading process of the reading apparatus are carried out concurrently with each other.

10. A sorting apparatus according to claim 8, wherein when the image capturing apparatus comprises a plurality of image capturing apparatus of different specifications, the sorting apparatus sorts the image capturing instruction information into a processing order so as to minimize a period of time required by image capturing processes carried out by the image capturing apparatus of different specifications.

11. A sorting apparatus according to claim 8, wherein the sorting apparatus sorts the image capturing instruction information into a processing order so as to minimize a period of time required to change an imaging posture of the subject for the image capturing apparatus.

12. A non-transitory computer-readable medium storing a program for being executed by a sorting apparatus to control an image capturing apparatus according to image capturing instruction information for capturing a plurality of radiation images of a subject, wherein the image capturing apparatus captures each of the radiation images of the subject by irradiating the subject with a radiation emitted from a radiation source, and the image capturing instruction information is supplied by a supply apparatus, the program comprising the steps of:
sorting the image capturing instruction information supplied from the supply apparatus, into a predetermined processing order; and
controlling the image capturing apparatus to capture the radiation images of the subject according to the processing order of the sorted image capturing instruction information; and
wherein the sorting apparatus receives the instruction information for capturing the plurality of radiation images as a plurality of instructions in a first sequence and sorts the plurality of instructions into the predetermined processing order, said predetermined processing order being different than the first sequence.

13. The non-transitory computer-readable medium storing the program according to claim 12, wherein the image capturing apparatus comprises:
a first image capturing apparatus for recording radiation image information in a first radiation conversion panel incorporated in the first image capturing apparatus by irradiating the first radiation conversion panel with the radiation through the subject; and
a second image capturing apparatus for recording radiation image information in a second radiation conversion panel by irradiating the second radiation conversion panel with the radiation through the subject, and reading the radiation image information from the second radiation conversion panel; and
wherein when a reading apparatus which is loaded with the second radiation conversion panel is further provided for reading the radiation image information recorded in the second radiation conversion panel, in the step of sorting the image capturing instruction information, the processing order is set such that after an image capturing process of the second image capturing apparatus is carried out, an image capturing process of the first image capturing apparatus and a reading process of the reading apparatus are carried out concurrently with each other.

14. The non-transitory computer-readable medium storing the program according to claim 12, wherein when the image capturing apparatus comprises a plurality of image capturing apparatus of different specifications, in the step of sorting the image capturing instruction information, the image capturing instruction information is sorted into a processing order so as to minimize a period of time required by image capturing processes carried out by the image capturing apparatus of different specifications.

15. The non-transitory computer-readable medium storing the program according to claim 12, wherein in the step of sorting the image capturing instruction information, the image capturing instruction information is sorted into a processing order so as to minimize a period of time required to change an imaging posture of the subject for the image capturing apparatus.

16. A radiation image capturing method for use in a case where an image capturing apparatus for capturing a radiation image of a subject by irradiating the subject with a radiation emitted from a radiation source, and a supply apparatus for supplying image capturing instruction information for capturing a plurality of radiation images of the subject are provided, the method comprising the steps of:

sorting, by a sorting apparatus, the image capturing instruction information supplied from the supply apparatus, into a predetermined processing order; and controlling, by the sorting apparatus, the image capturing apparatus to capture the radiation images of the subject according to the processing order of the sorted image capturing instruction information; and wherein the sorting apparatus receives the instruction information for capturing the plurality of radiation images as a plurality of instructions in a first sequence and sorts the plurality of instructions into the predetermined processing order, said predetermined processing order being different than the first sequence.

17. A method according to claim 16, wherein the image capturing apparatus comprises:

a first image capturing apparatus for recording radiation image information in a first radiation conversion panel incorporated in the first image capturing apparatus by irradiating the first radiation conversion panel with the radiation through the subject; and a second image capturing apparatus for recording radiation image information in a second radiation conversion panel by irradiating the second radiation conversion panel with the radiation through the subject, and reading the radiation image information from the second radiation conversion panel; and when a reading apparatus which is loaded with the second radiation conversion panel is further provided for reading the radiation image information recorded in the second radiation conversion panel, the method further comprises the step of setting, by the sorting apparatus, the processing order such that after an image capturing process of the second image capturing apparatus is carried out, an image capturing process of the first image capturing apparatus and a reading process of the reading apparatus are carried out concurrently with each other.

18. A method according to claim 16, when the image capturing apparatus comprises a plurality of image capturing apparatus of different specifications, further comprising the step of sorting the image capturing instruction information into a processing order so as to minimize a period of time required by image capturing processes carried out by the image capturing apparatus of different specifications.

19. A method according to claim 16, further comprising the step of sorting the image capturing instruction information into a processing order so as to minimize a period of time required to change an imaging posture of the subject for the image capturing apparatus.

* * * * *